US006403621B1

(12) United States Patent
Owen et al.

(10) Patent No.: US 6,403,621 B1
(45) Date of Patent: Jun. 11, 2002

(54) METHOD FOR PROTECTING PLANTS

(75) Inventors: Kirsty Joan Owen, Concord; Brian James Deverall, Hunters Hill, both of (AU)

(73) Assignee: Syngenta Crop Protection, Inc., Greensboro, NC (US)

( * ) Notice: Subject to any disclaimer, the term of this patent is extended or adjusted under 35 U.S.C. 154(b) by 0 days.

(21) Appl. No.: 09/486,520

(22) PCT Filed: Aug. 25, 1998

(86) PCT No.: PCT/EP98/05388

§ 371 (c)(1),
(2), (4) Date: Feb. 28, 2000

(87) PCT Pub. No.: WO99/09827

PCT Pub. Date: Mar. 4, 1999

(30) Foreign Application Priority Data

Aug. 27, 1997 (GB) .............................................. 9718036

(51) Int. Cl.[7] .......................... A01N 43/82; A01N 43/40
(52) U.S. Cl. ....................................... 514/361; 514/338
(58) Field of Search .................................. 514/361, 338

(56) References Cited

U.S. PATENT DOCUMENTS

| 4,968,344 | A |   | 11/1990 | Kunz et al. ..................... 71/94 |
| 5,190,928 | A |   | 3/1993 | Schurter et al. ............... 514/63 |
| 5,616,590 | A |   | 4/1997 | Maetzke ...................... 514/301 |
| 5,814,629 | A |   | 9/1998 | Stanetty et al. .......... 514/234.2 |
| 5,945,437 | A | * | 8/1999 | Ruess et al. ................. 514/361 |

OTHER PUBLICATIONS

Pesticide Science, vol. 50, pp. 275–282, 1997, XP–000732173.
Chemical Abstract 217975, XP 002087112 (Applied Biochemistry and Biology, vol. 33, No. 3, pp. 329–333, 1997).

* cited by examiner

*Primary Examiner*—Allen J. Robinson
(74) *Attorney, Agent, or Firm*—William A. Teoli, Jr.; Rose M. Allen

(57) ABSTRACT

A method of protecting plants against attack by nematodes which comprises applying an effective amount to the plants, to parts of the plants and/or to the locus of the plants a compound having plant immunizing properties; such compounds are for example isonicotinic acid-derivatives, benzo-1,2,3-thiadiazole-derivatives, pyrido-1,2,3-thiadiazole-derivatives and thieno-1,2,3-thiadiazole-derivatives.

8 Claims, No Drawings

METHOD FOR PROTECTING PLANTS

This application is a 371 of PCT/EP98/05388, filed Aug. 25, 1998.

The present invention relates to a method of protecting plants against attack by nematodes which comprises applying an effective amount to the plants, to parts of the plants and/or to the locus of the plants a compound having plant immunizing properties.

It is known that compounds having plant immunizing properties in general activate the plant's own latent defence system against pathogenic microbial influences and accordingly are able to protect the plant against pathogenic microorganism such as bacteria and fungi. Such compounds are for example isonicotinic acid-derivatives (U.S. Pat. No. 4,968,344), benzo-1,2,3-thiadiazole-derivatives (U.S. Pat. No. 5,190,928), pyrido-1,2,3-thiadiazole-derivatives (U.S. Pat. No. 5,616,590) and thieno-1,2,3-thiadiazole-derivatives (EP-A-780,394). Benzoisothiazole-derivatives with nematicidal activities, but having no plant immunizing properties have been disclosed in U.S. Pat. No. 5,447,945.

Surprisingly it has now been found that compounds with plant immunizing properties effectively protect plants against attack by nematodes of various species and therefore are suitable for practical agricultural purposes, e.g. for protecting crop plants against attack by nematodes.

Particularly suitable for this purpose are benzo-1,2,3-thiadiazole-derivatives of formula I

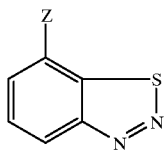

I

Within this group of compounds, it is believed that the active principle is the compound of formula I, wherein Z is COOH, i.e. 1,2,3-benzothiazole-7-carboxylic acid or its salt. Accordingly, all the compounds of formula I, wherein Z is a group which may undergo conversion to the carboxylic group, be it in the plant, on the plant or in the soil, are encompassed by this invention; particularly compounds of formula I, wherein Z is a $C_1$ group to which there are bonded 1–3 halogen atoms or 1–3 substituted or unsubstituted hetero atoms O, S and/or N, in free form or in salt form.

Examples are benzo-1,2,3-thiadiazole carboxylic acid and its derivatives, like -carboxylic esters, -orthoesters, -thioesters, -amides, -thioamides, -iminoethers, -amidines, -imidic acids, -hydroxamic acids and trihalomethyl.

Of the compounds of formula I, preference is given to those wherein

Z is CN, COOH or a salt thereof, CO—$OC_1$-$C_6$alkyl or CO—$SC_1$-$C_6$alkyl, CS—$OC_1$-$C_6$alkyl, CO—$NHC_1$-$C_6$alkyl, CO—$N(C_1$-$C_6$alkyl$)_2$, or CS—$SC_1$-$C_6$alkyl;

particularly preferred are compounds, wherein

Z is COOH or a salt thereof, CN, $COOCH_3$ or most preferably $COSCH_3$.

Preferred salts are alkali metal and alkaline earth metal salts, especially lithium, sodium, potassium, magnesium or calcium salts, and also organic salts, especially salts of salt-forming amines, for example trimethylamine, triethylamine, N,N-dimethylaniline, pyridine, triethanolamine, morpholine.

The method according to the invention is distinguished by an effective control of soil nematodes, is well tolerated by plants and environmentally friendly and, due to the low toxicity of the compounds, safe for users. Nematodes the attack of which to crop plants is controlled by the method according to the invention are soil nematodes that parasitise roots, for example nematodes of the genera Heterodera and Globodera (cystogenic nematodes), Meloidogyne (root-knot nematodes), Radopholus, Pratylenchus, Tylenchulus, Longidorus, Trichodorus, Xiphinema, Ditylenchus (stem parasites), Aphelenchoides (leaf nematodes), and Anguina (blossom nematodes). The method is particularly suitable against the attack of particularly harmful nematode species of the genus Meloidogyne, for example Meloidogyne incognita, and of the genus Heterodera, for example Heterodera glycines (soybean cyst nematode).

Target crops for the areas of indication disclosed herein comprise within the scope of the present invention e.g. the following species of plants: cereals (wheat, barley, rye, oats, rice, sorghum and related crops); beet (sugar beet and fodder beet); pomes, stone fruit and soft fruit (apples, pears, plums, peaches, almonds, cherries, strawberries, raspberries and blackberries); leguminous plants (beans, lentils, peas, soybeans); oil plants (rape, mustard, poppy, olives, sunflowers, coconut, castor oil plants, cocoa beans, groundnuts); cucumber.

Suitable carriers and adjuvants can be solid or liquid and are the substances ordinarily employed in formulation technology, e.g. natural or regenerated mineral substances, solvents, dispersants, wetting agents, tackifiers, thickeners, binders or fertilisers. Advantageous rates of application of the active ingredient mixture are normally from 0.1 to 10 kg of active ingredient (a.i.) per hectare, preferably from 100 g to 1000 g a.i./ha, especially from 250 g to 700 g a.i./ha. In the case of the treatment of seed, the rates of application are from 0.5 g to 1000 g, preferably from 5 g to 100 g, a.i. per 100 kg of seed. The formulations are prepared in known manner, e.g. by homogeneously mixing and/or grinding the active ingredients with extenders, e.g. solvents, solid carriers and surfactants. Suitable solvents are: aromatic hydrocarbons, preferably the fractions containing 8 to 12 carbon atoms, e.g. xylene mixtures or substituted naphthalenes, phthalates, such as dibutyl phthalate or dioctyl phthalate, aliphatic hydrocarbons, such as cyclohexane or paraffins, alcohols and glycols and their ethers and esters, such as ethanol, ethylene glycol, ethylene glycol monomethyl or monoethyl ether, ketones, such as cyclohexanone, strongly polar solvents, such as N-methyl-2-pyrrolidone, dimethyl sulfoxide or dimethylformamide, as well as vegetable oils or epoxidised vegetable oils, such as epoxidised coconut oil or soybean oil; or water. The solid carriers used, e.g. for dusts and dispersible powders, are normally natural mineral fillers, such as calcite, talcum, kaolin, montmorillonite or attapulgite. In order to improve the physical properties it is also possible to add highly dispersed silicic acid or highly dispersed absorbent polymers. Suitable granulated adsorptive carriers are porous types, for example pumice, broken brick, sepiolite or bentonite, and suitable nonsorbent carriers are, for example, calcite or sand. In addition, a great number of pregranulated materials of inorganic or organic nature can be used, e.g. especially dolomite or pulverised plant residues.

Depending upon the nature of the active ingredient to be formulated, suitable surface-active compounds are nonionic, cationic and/or anionic surfactants having good emulsifying, dispersing and wetting properties. Particularly advantageous application-promoting adjuvants are also natural or synthetic phospholipids of the cephalin and lecithin series, e.g. phosphatidylethanolamine, phosphatidylserine, phosphatidylglycerol and lysolecithin. plants (marrows, cucumber, melons); fibre plants (cotton, flax, hemp, jute); citrus fruit (oranges, lemons, grapefruit, mandarins); vegetables (spinach, lettuce, asparagus, cabbages, carrots, onions, tomatoes, potatoes, paprika); lauraceae (avocados, cinnamon, camphor); or plants such as maize, tobacco, nuts, coffee, sugar cane, tea, vines, hops, bananas and natural rubber plants, as well as ornamentals (flowers, shrubs, broad-leaved trees and evergreens, such as conifers). This list does not represent any limitation. The method of the invention is particularly suitable for treating vegetables as tomatoes, soybean, carrots, potatoes and beet, as well as citrus fruit, vines, tobacco, mango and bananas.

A preferred method of applying the active ingredient is application to the parts of the plants that are above the soil, especially to the leaves (foliar application). The frequency and rate of application depend upon the biological and climatic living conditions of the pathogen. The active ingredients can, however, also penetrate the plant through the roots via the soil or via the water (systemic action) if the locus of the plant is impregnated with a liquid formulation (e.g. in rice culture) or if the substances are introduced in solid form into the soil, e.g. in the form of granules (soil application). In order to treat seed, the compounds can also be applied to the seeds (coating), either by impregnating the tubers or grains with a liquid formulation, or by coating them with an already combined wet or dry formulation. In addition, in special cases, other methods of application to plants are possible, for example treatment directed at the buds or the fruit trusses. The compounds of formula I may be applied together with further active ingredients, for example, insecticides, fungicides, bactericides, nematicides, molluscicides or other plant activators. Combinations with other nematicides may exhibit synergistic effects.

The compounds of the invention are generally used in form of a composition together with the adjuvants conventionally employed in formulation technology. They are formulated in known manner e.g. into emulsifiable concentrates, directly sprayable or dilutable solutions, dilute emulsions, wettable powders, soluble powders, dusts, granules, and also encapsulations in e.g. polymer substances. As with the nature of the compositions, the methods of application, such as spraying, dusting, scattering or pouring, are chosen in accordance with the intended objectives and the prevailing circumstances.

The compositions generally comprise 0.1 to 99%, preferably 0.1 to 95%, of active ingredients, 99.9 to 1%, preferably 99.9 to 5%, of a solid or liquid adjuvant and 0 to 25%, preferably 0.1 to 25%, of a surfactant.

Whereas commercial products will preferably be formulated as concentrates, the end user will normally employ dilute formulations.

The following Examples serve to illustrate the invention

FORMULATION EXAMPLES

| Wettable powders | a) | b) | c) |
|---|---|---|---|
| active ingredient | 25% | 50% | 75% |
| sodium lignosulfonate | 5% | 5% | — |
| sodium laurylsulfate | 3% | — | 5% |
| sodium diisobutylnaphthalenesulfonate | — | 6% | 10% |
| octylphenol polyethylene glycol ether (7–8 mol of ethylene oxide) | — | 2% | — |

-continued

| Wettable powders | a) | b) | c) |
|---|---|---|---|
| highly dispersed silicic acid | 5% | 10% | 10% |
| kaolin | 62% | 27% | — |

The active ingredient is thoroughly mixed with the adjuvants and the mixture is thoroughly ground in a suitable mill, affording wettable powders which can be diluted with water to give suspensions of the desired concentration.

| Emulsifiable concentrate | |
|---|---|
| active ingredient | 10% |
| octylphenol polyethylene glycol ether (4–5 mol of ethylene oxide) | 3% |
| calcium dodecylbenzenesulfonate | 3% |
| castor oil polyglycol ether (35 mol of ethylene oxide) | 4% |
| cyclohexanone | 30% |
| xylene mixture | 50% |

Emulsions of any required dilution, which can be used in plant protection, can be obtained from this concentrate by dilution with water.

| Extruder granules | |
|---|---|
| active ingredient | 15% |
| sodium lignosulfonate | 2% |
| carboxymethylcellulose | 1% |
| kaolin | 82% |

The active ingredient is mixed and ground with the adjuvants, and the mixture is moistened with water. The mixture is extruded and then dried in a stream of air.

| Coated granules | |
|---|---|
| active ingredient | 8% |
| polyethylene glycol (mol. wt. 200) | 3% |
| kaolin | 89% |

The finely ground active ingredient is uniformly applied, in a mixer, to the kaolin moistened with polyethylene glycol. Non-dusty coated granules are obtained in this manner.

| Suspension concentrate | |
|---|---|
| active ingredient | 40% |
| propylene glycol | 10% |
| nonylphenol polyethylene glycol ether (15 mol of ethylene oxide) | 6% |
| sodium lignosulfonate | 10% |
| carboxymethylcellulose | 1% |
| silicone oil (in the form of a 75% emulsion in water) | 1% |
| water | 32% |

The finely ground active ingredient is intimately mixed with the adjuvants, giving a suspensions concentrate from which suspensions of any desired dilution can be obtained by dilution with water.

BIOLOGICAL EXAMPLES

Materials and Methods

Nematodes

Root-knot nematodes (Meloidogyne spp.) are cultured on tobacco or tomato. Root-knot nematode eggs are collected from these plants and hatched for inoculation of the grapevines using the standard method. Nematode eggs are collected from the inoculated grapevines by agitating clean root pieces in 0,8% NaOCl for four minutes. The roots are washed on a bank of three sieves and eggs collected on a 25 $\mu$m sieve. The eggs are washed into 100 ml of water and the number of eggs in a 20 ml sub-sample is estimated using a Doncaster dish. Galling is assessed in grapevine roots before egg counts. The roots are assessed with the naked eye for percentage of galls on the roots.

Grapevines

Uniformly developed rooted hardwood grapevine cuttings, variety Cabernet Sauvignon (Vitis vinifera), are planted into 20 cm diameter pots (one plant per pot) containing a pasteurised potting mix consisting of 50:50 coarse sand and peat. (Prior to pasteurisation, 300 g of fertiliser is added to each 50 liter bin of potting mix. The fertiliser consisted of 1000 g single superphosphate, 200 g ammonium nitrate, 150 g potassium sulphate, 100 g ferrous sulphate, 3000 g dolomite lime and 1500 g lime). The grapevines are grown in a glasshouse at 19–24° C. The plants are watered on alternate days, and fertilised weekly with a water soluble fertiliser. Grapevines are inoculated with 1000 juveniles of a mixed population of root-knot nematodes (Meloidogyne javanica and M. arenaria) 4 weeks after planting. The nematodes are pipetted into two 2cm deep holes at the base of the plant. Grapevine roots are harvested for nematode egg counts 10 weeks after inoculation (described below).

Application of Active Ingredient Acibenzolar-S-methyl (Compound of Formula I Wherein Z is COSCH$_3$)

Acibenzolar-S-methyl (which is benzo(1,2,3)thiadiazole-7-carbothioic acid S-methyl ester, a plant activator from NOVARTIS) is formulated as a 50% water dispersible granule, diluted to 50 mg per liter of spray mixture and sprayed onto the leaves of the grapevines (using a hand-held sprayer) until the point of run-off.

Two series of experiments have been conducted.

a) cumulative applications: In the first series, acibenzolar-S-methyl is applied to the plants once, twice or three times. The single treatment of acibenzolar-S-methyl is applied one week before inoculation; the double treatment is applied one week before inoculation and at the same time as inoculation; for the third treatment acibenzolar-S-methyl is applied one week before inoculation, at inoculation and one week after inoculation.

b) single applications: A second series of experiments tested only single applications of acibenzolar-S-methyl either five days before inoculation, at the same time as inoculation or five days after inoculation. Both series of experiments have been completed twice. Water is used as the control treatment in each series.

Results

The tables indicate the number of eggs produced by Meloidogyne spp in a 20 ml sub-sample, and the percentage galling on roots, resp.

TABLE 1

Cumulative applications one week before inoculation, at inoculation and/or one week after inoculation

| Application | Number of eggs (number of replicates per treatment) | |
|---|---|---|
| | first experiment | second experiment |
| control | 4320 (8) | 240 (7) |
| one application | 1520 (8) | 150 (7) |
| two applications | 740 (7) | 100 (7) |
| three applications | 1400 (6) | 20 (7) |

TABLE 2

Single applications 5 days before inoculation, at inoculation or 5 days after inoculation

| Application | Number of eggs (number of replicates per treatment) | |
|---|---|---|
| | first experiment | second experiment |
| control | 3010 (6) | 1120 (7) |
| five days before inoculation | 930 (8) | 630 (7) |
| at inoculation | 720 (8) | 620 (6) |
| five days after inoculation | 910 (8) | 770 (8) |

TABLE 3

Single applications 5 days before inoculation, at inoculation or 5 days after inoculation

| Application | Mean percentage galling (number of replicates per treatment) | |
|---|---|---|
| | first experiment | second experiment |
| control | 10 (6) | 5 (7) |
| five days before inoculation | 0.6 (8) | 2 (7) |
| at inoculation | 2.3 (8) | 3 (6) |
| five days after inoculation | 1.1 (8) | 4 (8) |

There are no significant differences in appearance of grapevines at harvest. No phytotoxicity is observed and no difference in root fresh weights or the fresh weight of the foliage and stems are seen.

Good effects for protecting plants against attack by nematodes are also found by applying acibenzolar-S-methyl on tomatoes, soybean, carrots, potatoes and beet.

Direct Effect of Acibenzolar-S-methyl onto Nematodes

Eggs and juvenile root-knot nematodes are placed into aqueous solutions of acibenzolar-S-methyl (1, 10, 20 and 50 ppm active ingredient). No effect is observed on egg hatching and viability on those eggs and juvenils on penetration of those nematodes into tomato roots and on the number of eggs produced by those nematodes on tomatoes.

What is claimed is:

1. A method of treating plants attacked by nematodes which comprises applying to the plants and/or the locus of the plants infested with nematodes, a benzo-1,2,3-thiadiazole-derivative of formula I

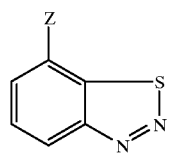

wherein

Z is a group which may undergo conversion to the carboxylic group COOH, especially a $C_1$ group to which there are bonded 1–3 halogen atoms or 1–3 substituted or unsubstituted hetero atoms O, S and/or N, in free form or in salt form.

2. A method according to claim 1, wherein in the compound of formula I

Z is CN, COOH or a salt thereof, CO—O$C_1$–$C_6$alkyl or CO—S$C_1$–$C_6$alkyl, CS—O$C_1$–$C_6$alkyl, CO—NH$C_1$–$C_6$alkyl, CO—N($C_1$–$C_6$alkyl)$_2$, or CS—S$C_1$–$C_6$alkyl.

3. A method according to claim 2, wherein in the compound of formula I

Z is COOH or a salt thereof, CN, COOCH$_3$ or COSCH$_3$.

4. A method according to claim 3 wherein in the compound of formula I

Z is COSCH$_3$.

5. A method according to claim 1, wherein the nematodes are parasites of plants.

6. A method according to claim 5, wherein the nematodes are of the genus Heterodera.

7. A method according to claim 5, wherein the nematodes are of the genus Meloidogyne.

8. A method according to claim 1, wherein the compound is applied to vegetables, citrus fruit, vines, tobacco and bananas.

* * * * *